US00PP14145P39

(12) United States Plant Patent
Heidgen

(10) Patent No.: US PP14,145 P3
(45) Date of Patent: Sep. 16, 2003

(54) GERANIUM PLANT NAMED 'MRS. PETERS'

(76) Inventor: Charles F. Heidgen, 821 Walnut St., Batavia, IL (US) 60510

( * ) Notice: Subject to any disclaimer, the term of this patent is extended or adjusted under 35 U.S.C. 154(b) by 0 days.

(21) Appl. No.: 09/969,331

(22) Filed: Oct. 3, 2001

(65) Prior Publication Data

US 2003/0066115 P1 Apr. 3, 2003

(51) Int. Cl.[7] ..... A01H 5/00

(52) U.S. Cl. ..... Plt./328

(58) Field of Search ..... Plt./328, 325

*Primary Examiner*—Kent Bell

(57) ABSTRACT

A geranium plant named 'Mrs. Peters', from a naturally occurring branch sport of 'Hills of Snow' (unpatented) identified by its medium to vigorous growth habit; its medium-sized, grey green foliage with creamy white edges; and its prolific flowering characteristic. The blooms are medium sized, double flowers that are a distinct true pink color that gradually fades to white at the center of each of the blooms.

1 Drawing Sheet

BACKGROUND OF THE INVENTION

The present invention relates to a new and distinct cultivar of Geranium plant, botanically known as *Pelargonium*× *hortorum* and hereinafter referred to by the name 'Mrs. Peters'.

The new and improved Geranium is a result of a planned breeding program as performed by me in my greenhouse at 821 Walnut Street, Batavia, Ill. My breeding program began in March 1977, and has been ongoing since that time.

The new Geranium originated in July of 1998 and the instant plant was a naturally occurring branch sport of the unpatented *Pelargonium*×*hortorum* 'Hills of Snow', which is a green and white variegated foliaged geranium variety that has a narrow border of white on silvery gray green leaves. The instant plant was discovered on only one single plant of a cultivated planting of 'Hills of Snow'.

Upon recognition of the outstanding characteristics of this plant, it was selected and was set aside for further observation and testing and was subsequently named 'Mrs. Peters.' Asexual reproduction of the new cultivar by terminal cuttings taken at Batavia, Ill., has shown that the unique features of this new Geranium are stable and reproduced true to type in successive generations of asexual reproduction.

SUMMARY OF THE INVENTION

The new and distinguishing characteristics of 'Mrs. Peters' reside primarily in its medium to vigorous growth habit, its prolific blooming characteristic and its medium-sized, grey green foliage with creamy white edges. This geranium also has medium sized, double flowers with a true pink color that fades to white at the center, as well as heat tolerance. This plant might be seen as a novel and desirable introduction within the industry by a combination of desired traits including:

Being particularly adapted to culture in the ground or in pots due to its medium to vigorous growth habit, dense leafy canopy and its tendency to branch prolifically. Forming a bushy plant mass in approximately 7–9 weeks from one plantlet, and a plant that is not stretched or leggy, but rather, a mounded and dense plant.

Having a generous amount of foliage, with grey green coloration and contrasting, creamy white variegated edges on each of the medium sized leaves and of higher than normal density.

Presenting a high number of well filled umbels of varied states of maturity placed well above the foliage mass, and having a true pink flower coloration, that fades to white at the center, which is distinctively, contrastingly highlighted over and against the grey green, variegated foliage.

Having a large number of umbels with a generous number of open, double petal flowers of a medium size and appearance, borne on pedicels which present the flowers in a dense arrangement to form umbels having a globular and somewhat fluffy appearing shape.

Presenting a large number of umbels which also vary in stage of maturity, which gives the plant an attractive appearance for an extended period of time, rather than being one that blooms in discontinuous flushes.

The color definitions to follow have been taken from The Royal Horticultural Colour Chart of The Royal Horticultural Society, London, where presented by the letters RHS followed by a color grouping indication, the number indicating the color patch and the letter indicating the shade, except where color definitions in general terms of ordinary meaning are presented. Plant descriptions were made from specimens in 5½" pots that were approximately 14 weeks of age and grown under greenhouse conditions during daylight hours in Batavia, Ill.

BRIEF DESCRIPTION OF THE DRAWING

The photograph depicts a market unit that has one market stage plant growing in a 5½" pot, in a stage of inflorescence. The plant is shown in a side view, depicting the characteristics of branching, leaves, leaf coloration and zonation, the number and varied stages of buds and flowers, and the positioning of the flower heads relative to the mass of the plant in the pot.

BOTANICAL DESCRIPTION OF THE PLANT

Botanical classification: *Pelargonium*×*hortorum.*

Market class: Zonal Geranium suitable for planting in the ground or in containers.

Market name: 'Mrs. Peters'.

Growth: 'Mrs. Peters' is a prolific blooming Geranium with double flowers and the truss or flower head is of medium size. The growth is upright in habit and given to branching freely.

Growth rate: Average, producing a typical 4½" flowering geranium in about 7 to 9 weeks from one 2¼" plantlet using standard commercial culture.

Blooming habit: Exceptionally profuse and continuously blooming plant throughout the year, outdoors during the frost-free period, or in the greenhouse; a mature 4½" pot commonly producing a range of 4 to 7 Umbels at one time, in varying states of maturity.

INFLORESCENCE

Umbels:

*Size.*—2⅝ to 3¼ inches across when the flowers are fully open.

*Count.*—4 to 7 present at one time.

*Shape.*—Rather dense, a somewhat fluffy appearing globe, as it opens.

*Number of flowers.*—Variable, range from approximately 13 to 29, average 14 to 20.

*Lasting quality.*—Average. Blooms last 5 to 8 days, possibly longer in cooler, dry weather.

Buds:

*Size.*—Short to medium length, average width.

*Color.*—RHS Yellow Green Group, 145 A, with RHS White Group 157 B edges.

*Form.*—Oval, slight point, but more rounded.

Flowers:

*Number.*—14 to 20.

*Form.*—Rather cupped to flat, as it opens fully.

*Size.*—Ranging from ⅞ inch to 1⅝ inches across a fully open flower.

Petals:

*Number.*—Ranging from 12 to 17.

*Size.*—Ranging from about 7/16 to ⅞ inches long and approximately ⅜ to 9/16 inches across.

*Shape.*—Obovate.

*Apex.*—Rounded.

*Base.*—Attenuate.

*Margin.*—Entire.

*Texture.*—Soft.

*Appearance.*—Bright.

*Color.*—Upper surface: RHS Red Group, 55 B main part and toward edge of the petal with a RHS White Group 155 D at the center towards the base. Lower surface: RHS Red Group, 56 C.

Petaloids:

*Number.*—Substantially absent, but may occur in number up to 8.

*Shape.*—Variable, often misshapen.

*Color.*—Upper surface: RHS Red Group, 55 C. Lower surface: RHS Red Group, 56 D.

*Size.*—3/16 to ⅜ inches long and ¼ to ⅝ inches wide.

Sepals:

*Number.*—Usually 5.

*Size.*—5/16 inch in length and ⅛ inch in width.

*Apex.*—Narrow.

*Margin.*—Entire.

*Color.*—Upper surface: RHS Green Group, 144 B. Lower surface: RHS Green Group, 143 C with RHS White Group 155 C at the outer edge.

Pedicel:

*Length.*—About ⅞ to ⅜ inches long.

*Color.*—RHS Yellow Green Group, 146 C.

Peduncle:

*Arises.*—From node, opposed to leaf petiole.

*Pubescence.*—Normal.

*Color.*—RHS Yellow Green Group, 144 A.

*Length.*—3¼ to 3 11/16 inches long.

REPRODUCTIVE ORGANS

Androecium:

*Stamens.*—Number — 4 to 8. Shape — Ribbon-like filaments jointed at bases. Color — Pale pink. Anther Attachment — versatile.

*Anthers.*—Number — 4 to 8. Shape — Normal, well developed. Color — Brown.

Gynoecium:

*Pistil.*—Number — One, compound. Length — Within the range of 3/32 to 5/32 inches.

*Stigma.*—Color — Rose pink.

*Style.*—Color — Pink fading to white toward ovary.

*Ovary.*—Size — Approximately 1/32 to 1/16 inches long.

Fertility: Pollen is not produced and viable seed is rarely produced.

Behavior: Once the plant begins to bloom, it has a prolific blooming habit and yields a striking display of medium sized, double flowers of true pink color that fades to white at the center of each flower against its medium sized, grey green leaves with creamy white, variegated edges.

General observations: Inflorescence is of medium size and of rather dense heads of double flowers, which are an attractive contrast to the grey green foliage with creamy white variegated edges, approximately 3 inches in diameter. At optimum stage of opening, the double flowers are distinctive and striking with their true pink coloration that fades to white at the center. Flowers have high heat tolerance when compared to other varieties, known to me.

STEM

Thickness: 2/16 to 5/16 inches in diameter.

Internodes: ⅜ to 15/16 inches in length.

Branching: Very free breaking.

Attitude: Upright, bushy habit.

Color: RHS Yellow-Green Group, 145 A.

FOLIAGE

Leaves:

*Quantity.*—Abundant.

*Shape.*—Reniform.

*Size.*—Medium, largest leaves range from about 2⅝ to 3⅝ inches across.

*Margin.*—Crenate.

*Texture.*—Somewhat pubescent, matt texture.

*Coloration.*—Upper surface: RHS Greyed Green Group, 191 A, with an irregularly shaped variegation of RHS White Group 155 A on the edge of each leaf. The variegation ranges in width from 1/16 to ⅞ inches, beginning at the edge of the leaf and going toward the center of each leaf. Lower surface: RHS Greyed Green Group, 191 B with an irregular variegation of RHS White Group 155 A on the edge. Shape and width of variegation on lower surface is identical to upper surface.

Petioles:

*Texture.*—Lightly pubescent.

*Length.*—Approximately 1⅜ to 2⅛ inches.

*Color.*—RHS Yellow Green Group, 146 B.

Plant height (to top of foliage): 6¾ inches.
Plant width: 12⅛ inches.
Disease resistance: Resistance to pathogens common to Pelargonium observed to be good.

'Mrs. Peters' is comparable to 'Wilhelm Languth' (unpatented) with which it shares market class, but is easily distinguishable therefrom in terms of flower color; 'Mrs. Peters' having true pink petal coloration which fades to white at the center of each flower, while the petals of 'Wilhelm Languth' (unpatented) are scarlet red with no gradation of color and no white eye. 'Mrs. Peters' is readily distinguished from 'Peaches' (U.S. Plant Pat. No. 10,421) by having double flowers of true pink petal coloration fading to a white center, in addition to a grey green leaf coloration with a bold, creamy white, irregular variegation on the edges of each leaf.

I claim:

1. A new and distinct variety of Geranium plant named 'Mrs. Peters', as herein illustrated and described.

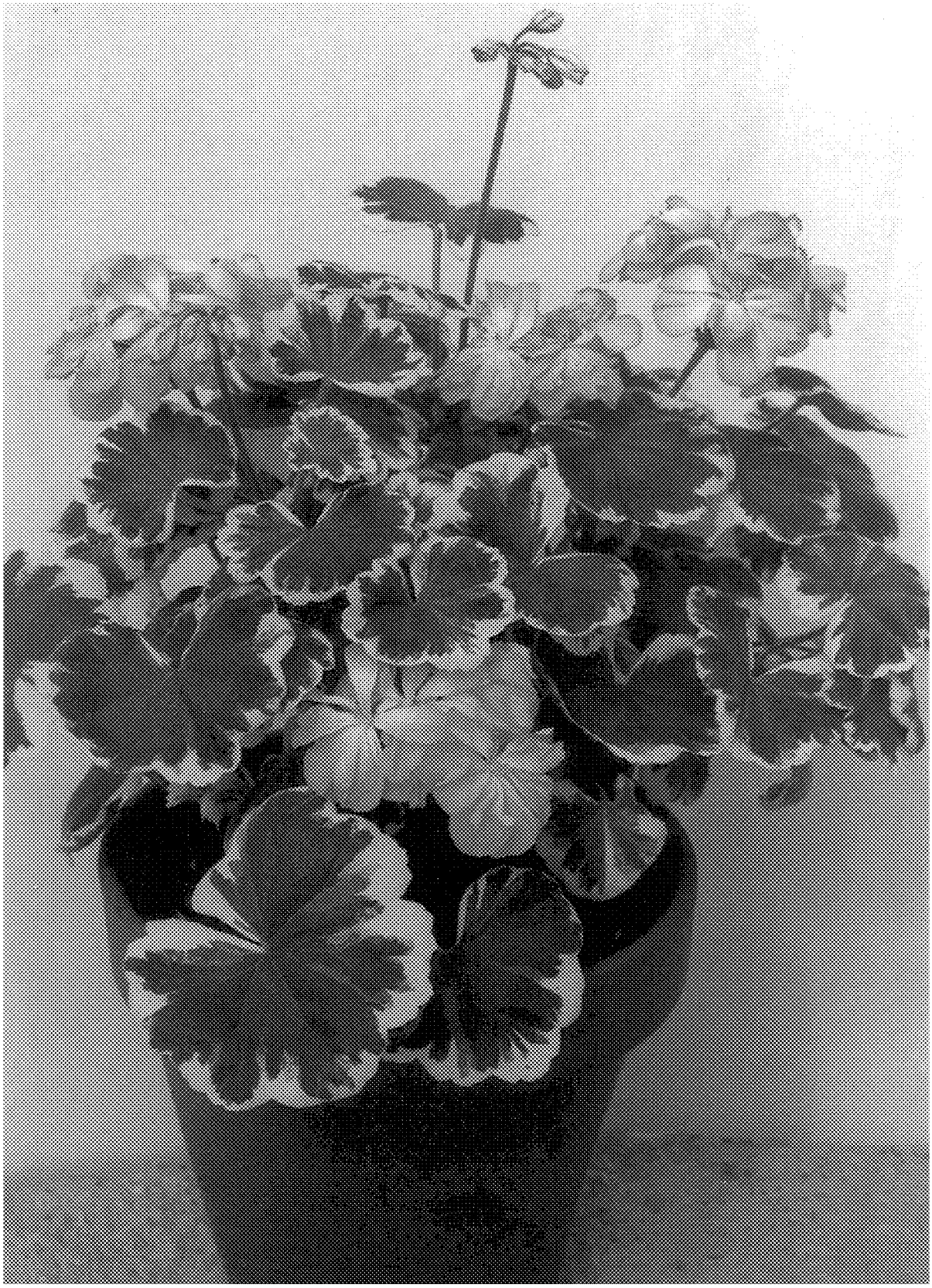

* * * * *